(12) United States Patent
Gwak et al.

(10) Patent No.: US 10,450,262 B2
(45) Date of Patent: Oct. 22, 2019

(54) METHOD FOR PURIFYING 1,4-DIAMINOBUTANE

(71) Applicant: CJ CHEILJEDANG CORPORATION, Seoul (KR)

(72) Inventors: Won Sik Gwak, Yongin-si (KR); Hong Xian Li, Seoul (KR); Hyun Ju Won, Pohang-si (KR); Hyo Hyoung Lee, Incheon (KR); Kyung Su Na, Gimpo-si (KR); Su Jin Park, Seoul (KR); Young Lyeol Yang, Seoul (KR); Hye Won Um, Suwon-si (KR); Chang Yub Oh, Yongin-si (KR); Kyoung Min Lee, Seoul (KR)

(73) Assignee: CJ CHEILJEDANG CORPORATION, Jung-Gu, Seoul (KR)

( * ) Notice: Subject to any disclaimer, the term of this patent is extended or adjusted under 35 U.S.C. 154(b) by 0 days.

(21) Appl. No.: 15/572,381

(22) PCT Filed: May 4, 2016

(86) PCT No.: PCT/KR2016/004686
§ 371 (c)(1),
(2) Date: Nov. 7, 2017

(87) PCT Pub. No.: WO2016/182257
PCT Pub. Date: Nov. 17, 2016

(65) Prior Publication Data
US 2018/0127351 A1    May 10, 2018

(30) Foreign Application Priority Data

May 8, 2015  (KR) .................. 10-2015-0064622

(51) Int. Cl.
*C07C 209/86* (2006.01)
*C07C 211/09* (2006.01)
(Continued)

(52) U.S. Cl.
CPC .............. *C07C 209/86* (2013.01); *B01D 3/14* (2013.01); *C07C 209/84* (2013.01); *C07C 211/09* (2013.01); *C12P 13/001* (2013.01)

(58) Field of Classification Search
CPC ....... B01D 3/14; C07C 209/84; C07C 209/86; C07C 211/09; C12P 13/001
See application file for complete search history.

(56) References Cited

U.S. PATENT DOCUMENTS 8,334,411 B2 * 12/2012 Ito ..................... B01D 61/027
                                                    564/138
8,906,653 B2    12/2014 Volkert et al.
(Continued)

FOREIGN PATENT DOCUMENTS

EP    2263996 A1    12/2010
JP    S5839644 A     3/1983
(Continued)

OTHER PUBLICATIONS

Examination Report dated Jul. 3, 2018 of the Australian patent application No. 2016260500.
(Continued)

*Primary Examiner* — Sudhakar Katakam
*Assistant Examiner* — Jennifer C Sawyer
(74) *Attorney, Agent, or Firm* — Cantor Colburn LLP (57) ABSTRACT

A method for purifying 1,4-diaminobutane comprising the steps of: separating a second composition including carbonate salt of 1,4-diaminobutane from a first composition including carbonate salt of 1,4-diaminobutane by distillation; and removing carbonate from carbonate salt of 1,4-diaminobutane included in the second composition to recover 1,4-diaminobutane.

24 Claims, 1 Drawing Sheet

(51) Int. Cl.
*B01D 3/14* (2006.01)
*C07C 209/84* (2006.01)
*C12P 13/00* (2006.01)

(56) References Cited

U.S. PATENT DOCUMENTS

| | | |
|---|---|---|
| 8,927,774 B2 | 1/2015 | Gwak et al. |
| 2014/0213824 A1 | 7/2014 | Gwak et al. |

FOREIGN PATENT DOCUMENTS

| | | |
|---|---|---|
| JP | S62114943 A | 5/1987 |
| JP | 2012201817 A | 10/2012 |
| KR | 1020090107920 A | 10/2009 |
| KR | 1020100117084 A | 11/2010 |
| KR | 1020100133366 A | 12/2010 |
| KR | 1020140052189 A | 5/2014 |
| KR | 1020140115244 A | 9/2014 |
| TW | 200732280 | 7/1986 |
| WO | 2009092793 A2 | 7/2009 |
| WO | 2013028030 A2 | 2/2013 |
| WO | 2014065553 A1 | 5/2014 |
| WO | 2015025896 A1 | 2/2015 |

OTHER PUBLICATIONS

Zhi-Gang Qian, et al., "Metabolic Engineering of *Escherichia coli* for the Production of Putrescine: A Four Carbon Diamine", Biotechnology and Bioengineering, vol. 104, No. 4, Nov. 1, 2009, pp. 651-662.
International Search report for PCT/KR2016/004686, dated Aug. 11, 2016 (4 pages with translation).
Indian examination report dated Mar. 19, 2019 of the India patent application No. 201717039763, which corresponds to the above-identified patent application with English Translation.
Office Action dated Dec. 18, 2018, of the Japanese Patent Application No. 2018-510689, with English Translation.
Russian Office Action dated Sep. 27, 2018, of the Russian patent Application No. 2017141778, with English Translation.
Russian Search Report for Application No. 2017141778 with English Translation, 2018.

\* cited by examiner

METHOD FOR PURIFYING 1,4-DIAMINOBUTANE

TECHNICAL FIELD

One or more embodiments relate to a method of refining 1,4-diaminobutane.

BACKGROUND ART 1,4-diaminobutane (also referred to as putrescine) may be produced by using a chemical method or a biological method. The chemical method involves using a toxic material such as hydrogen cyanide or an expensive reaction catalyst. The biological method may include producing 1,4-diaminobutane by culturing a microorganism that produces 1,4-diaminobutane and refining the 1,4-diaminobutane from a fermented broth. Therefore, the biological method is environment-friendly, compared to the chemical method and does not use an expensive catalyst.

However, in the conventional biological method of producing 1,4-diaminobutane, the fermented broth includes a sulfate of 1,4-diaminobutane, and thus an alkali compound is added thereto to purify the sulfate, a large amount of by-products are produced, and additional purifying process of the by-products is needed.

Therefore, a simple and economic method that does not require addition of an alkali compound during the purifying process and that may reduce production of by-products is needed.

DETAILED DESCRIPTION OF THE INVENTION

Technical Problem

An aspect provides a novel method of purifying 1,4-diaminobutane.

Technical Solution

Additional aspects will be set forth in part in the description which follows and, in part, will be apparent from the description, or may be learned by practice of the presented embodiments.

Another aspect provides a method of purifying 1,4-diaminobutane includes: separating a second composition including carbonate salt of 1,4-diaminobutane from a first composition including carbonate salt of 1,4-diaminobutane by distillation; and removing carbonate from the carbonate salt of 1,4-diaminobutane included in the second composition to recover 1,4-diaminobutane.

Another aspect provides a method of purifying 1,4-diaminobutane includes: culturing a microorganism having an ability to produce 1,4-diaminobutane in a medium while being provided with a nitrogen source to produce carbonate salt of 1,4-diaminobutane; preparing a fermented broth or a concentrate thereof that includes the carbonate salt of 1,4-diaminobutane from the medium; separating a third composition including carbonate salt of 1,4-diaminobutane by distillation of the fermented broth or a concentrate thereof; and removing carbonate from the 1,4-diaminobutane carbonate included in the third composition to recover 1,4-diaminobutane.

Advantageous Effects of the Invention

When the purifying method according to one or more embodiments of the present disclosure is used, 1,4-diaminobutane may be easily obtained with a high yield from a composition including carbonate salt of 1,4-diaminobutane. Furthermore, since consumption of an alkali compound required in the purifying method is reduced along with a reduction in an amount of by-products, which generated an additional cost, a cost for the purifying method thus used may be decreased as well.

BEST MODE

Figure 1:
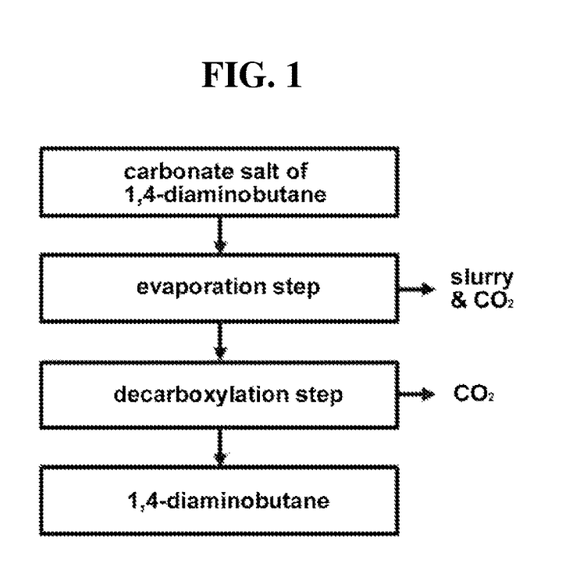
FIG. 1 is a schematic flowchart of a method of purifying 1,4-diaminobutane.
Figure 2:
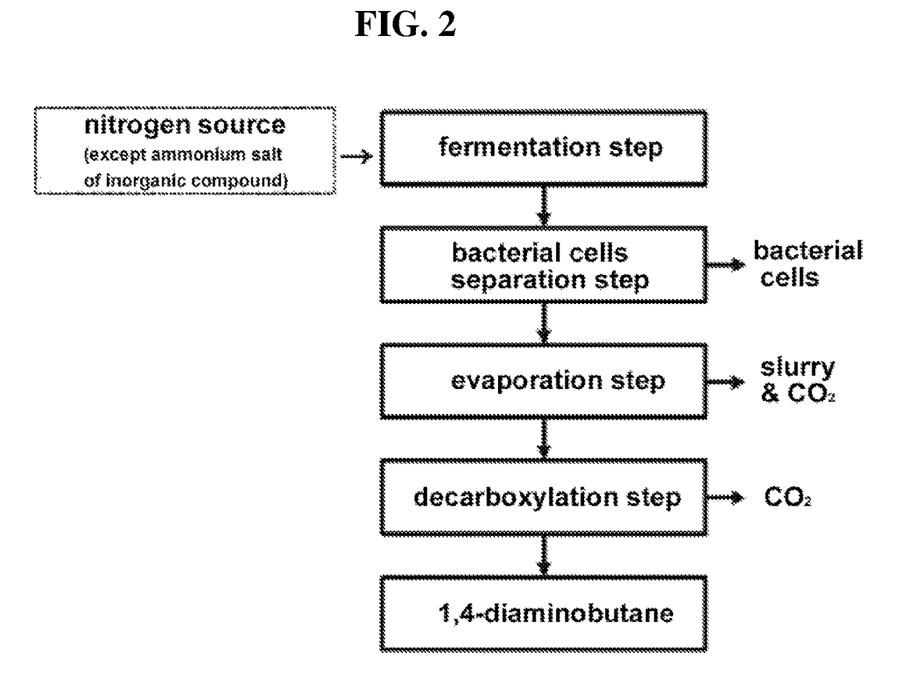
FIG. 2 is a flowchart of a method of purifying 1,4-diaminobutane including from fermentation step to decarboxylation step.

Hereinafter, a method of purifying 1,4-diaminobutane, according to an embodiment of the present disclosure, will be described in detail.

According to an aspect of the present disclosure, a method of purifying 1,4-diaminobutane includes: separating a second composition including carbonate salt of 1,4-diaminobutane from a first composition including carbonate salt of 1,4-diaminobutane by distillation; and removing carbonate from the carbonate salt of 1,4-diaminobutane included in the second composition to recover 1,4-diaminobutane.

In some embodiments of the purifying method, 1,4-diaminobutane may be easily refined by separating carbonate salt of 1,4-diaminobutane from a composition including carbonate salt of 1,4-diaminobutane and removing carbonate from the separated carbonate salt of 1,4-diaminobutane.

The purifying method does not involve addition of an additional base material, unlike a conventional purifying method, which includes adding a base material to a composition including carbonate salt of 1,4-diaminobutane before distillation to alkalify the composition and then performing the distillation. In this regard, when the method according to an embodiment of the present disclosure is used, a purifying process may be simplified and by-products produced from the method may be reduced.

In the purifying method, the carbonate salt of 1,4-diaminobutane refers to all types of salts that may be formed when 1,4-diaminobutane bonds with carbonate. In particular, the carbonate salt of 1,4-diaminobutane may be at least one selected from 1,4-diaminobutane carbonate ($PUT^{2+}CO_3^{2-}$, where PUT is 1,4-diaminobutane (putrescine)) and 1,4-diaminobutane bicarbonate ($PUT^{2+}(HCO_3^-)_2$).

In the purifying method, the first composition may be any composition including carbonate salt of 1,4-diaminobutane, or, in some embodiments, the first composition may be a fermented broth or a concentrate thereof, wherein the fermented broth is obtained by culturing a microorganism and includes carbonate salt of 1,4-diaminobutane.

In some embodiments of the purifying method, the fermented broth may be prepared through fermentation. The fermented broth may be prepared by culturing a microorganism, which may be, for example, a mutated microorganism.

For example, when a *Corynebacterium* genus microorganism is used, the fermented broth may be prepared by growing the microorganism on a cornmeal malt extract agar (CMA) solid medium, inoculating the microorganism into a spawn culture medium, and then culturing the microorganism by re-inoculating the microorganism to the main culture medium.

Types of microorganisms and fermentation conditions that may be used in the preparation of the fermented broth will be described in detail when the purifying method including the following culturing steps.

In the purifying method, the concentrate of the fermented broth may be prepared by concentrating the fermented broth including carbonate salt of 1,4-diaminobutane.

During the concentrating of the fermented broth, at least some of a solvent included in the fermented broth may be removed. Such removal of the at least some of the solvent may increase a concentration of carbonate salt of 1,4-diaminobutane in the fermented broth. The solvent being removed may be, for example, water. In the concentrating of the fermented broth including carbonate salt of 1,4-diaminobutane, about 50% or more, or, for example, about 60% or more, about 70% or more, or about 80% or more of an initial amount of the solvent in the fermented broth that is not concentrated may be removed.

When the fermented broth contains bacterial cells in the concentrating of the fermented broth, the concentrating of the fermented broth may be performed in a low temperature and reduced pressure environment to prevent destruction of bacterial cells.

In some embodiments of the purifying method, the concentrating of the fermented broth may be performed at a vapor temperature of about 100° C. or lower. That is, the concentrating of the fermented broth may be performed at a temperature of about 100° C. or lower at which vapor evaporates from the fermented broth. For example, the concentrating of the fermented broth may be performed at a vapor temperature in a range of about 10° C. to about 100° C., or, for example, about 30° C. to about 80° C., or about 45° C. to about 67° C. When the vapor temperature is within these ranges, the solvent may be easily removed.

Furthermore, the concentrating of the fermented broth may be performed at a reduced pressure of about 760 mmHg or lower. That is, the concentrating of the fermented broth may be performed at a pressure of about 760 mmHg or lower at which a pressure of vapor in equilibrium with the fermented broth is about 760 mmHg or lower. For example, the concentrating of the fermented broth may be performed at a pressure in a range of about 10 mmHg to about 760 mmHg, or, for example, about 40 mmHg to about 500 mmHg, or about 70 mmHg to about 200 mmHg. When the pressure is within these ranges, the solvent may be easily removed.

For example, the concentrate of the fermented broth may be performed at a vapor temperature in a range of about 10° C. to about 100° C. and a pressure in a range of about 10 mmHg to about 760 mmHg.

In the purifying method, the pH of the concentrate of the fermented broth may be about 10.0 or higher. Since the pH of the concentrate of the fermented broth is 10 or higher, a salt of 1,4-diaminobutane included in the fermented broth may be, for example, carbonate salt of 1,4-diaminobutane.

In the purifying method, about 70 wt % or more of carbonate salt of 1,4-diaminobutane in the first composition may be separated or removed by distillation. In some embodiments, about 75 wt % or more, or, for example, about 80 wt % or more, about 85 wt % or more, or about 90 wt % or more of carbonate salt of 1,4-diaminobutane in the first composition may be separated by the distillation. Furthermore, at least a part of carbon dioxide from carbonate salt of 1,4-diaminobutane in the first composition may be separated by the distillation.

In the purifying method, the second composition including carbonate salt of 1,4-diaminobutane may be separated from the first composition including 1,4-diaminobutane by the distillation at a vapor temperature in a range of about 30° C. to about 158° C., or, for example, about 40° C. to about 120° C. The second composition including carbonate salt of 1,4-diaminobutane may be separated with a high yield within the vapor temperature range.

In the purifying method, the second composition including carbonate salt of 1,4-diaminobutane may be separated from the first composition including 1,4-diaminobutane by the distillation at a vapor pressure in a range of about 10 mmHg to about 760 mmHg, or, for example, about 70 mmHg to about 200 mmHg. The second composition including carbonate salt of 1,4-diaminobutane may be separated with a high yield within the pressure range.

The second composition including carbonate salt of 1,4-diaminobutane, which is separated under the conditions of the temperature and the pressure described above, may be obtained in a liquid state by condensation or may be used in a vaporized state, without condensation, in the later steps.

In the purifying method, the second composition including carbonate salt of 1,4-diaminobutane that is separated by distillation may include carbonate salt of 1,4-diaminobutane and a solvent. For example, the second composition may only include carbonate salt of 1,4-diaminobutane and a solvent and may not include other components such as ions, amino acids, organic acids, protein, or bacterial cells.

In the purifying method, the pH of the second composition including carbonate salt of 1,4-diaminobutane may be about 10.0 or higher. Since the pH of the second composition including carbonate salt of 1,4-diaminobutane obtained from the first composition by distillation is about 10 or higher, an additional additive such as an alkali compound is not necessary to increase the pH of the second composition.

The second composition including carbonate salt of 1,4-diaminobutane obtained by distillation may include 1,4-diaminobutane bicarbonate and/or 1,4-diaminobutane carbonate. For example, the second composition including carbonate salt of 1,4-diaminobutane may include 1,4-diaminobutane bicarbonate as a main component or may include 1,4-diaminobutane carbonate as a main component. For example, the second composition including carbonate salt of 1,4-diaminobutane may include only 1,4-diaminobutane bicarbonate or may include only 1,4-diaminobutane carbonate in addition to a solvent. As used herein, the term "main component" denotes a composition having the highest content among components included in the composition other than a solvent.

In the purifying method, the second composition including carbonate salt of 1,4-diaminobutane may be in a gaseous state, a liquid state, or a mixed state thereof. A state of the second composition including carbonate salt of 1,4-diaminobutane may vary depending on required purifying conditions.

In some embodiments, vapor or condensate of the second composition including carbonate salt of 1,4-diaminobutane obtained by distillation in the separation process may be recovered. The separating of the second composition by distillation may be performed using a double jacketed reactor.

The removing of carbonate from the carbonate salt of 1,4-diaminobutane in the second composition to recover 1,4-diaminobutane may be performed by fractional distillation.

By the recovering of the 1,4-diaminobutane via fractional distillation from the second composition including carbonate salt of 1,4-diaminobutane, carbon dioxide may be separated from the carbonate salt of 1,4-diaminobutane, and 1,4-diaminobutane may be recovered.

For example, the second composition including carbonate salt of 1,4-diaminobutane may be separated from the first composition by distillation, condensed, and stored. Then, the separated second composition may be used in the recovering of 1,4-diaminobutane.

The second composition including carbonate salt of 1,4-diaminobutane may be stored in a reservoir disposed between a top of the reactor and a distillation column, but not limited thereto, and any storing method in the art may be used.

In some embodiments of the purifying method, the separating of the second composition including carbonate salt of 1,4-diaminobutane by distillation and the recovering of 1,4-diaminobutane by fractional distillation may be continuously performed. In other words, the second composition including carbonate salt of 1,4-diaminobutane may be separated from the first composition by distillation and at the same time the composition may be further separated into 1,4-diaminobutane and carbonate by fractional distillation to recover 1,4-diaminobutane. The 1,4-diaminobutane recovered by fractional distillation may be a final product.

In some embodiments of the purifying method, the fractional distillation may be performed at a vapor temperature in a range of about 100° C. to about 230° C. and a atmospheric pressure or higher, i.e., in a range of about 1 atm to about 5 atm, or, for example, at a vapor temperature in a range of 100° C. to about 158° C. and an atmospheric pressure. The 1,4-diaminobutane may be obtained with a high yield within these temperature and pressure ranges.

In some embodiments of the purifying method, the recovering of 1,4-diaminobutane may be performed using a distillation tower. For example, after preparing the second composition including carbonate salt of 1,4-diaminobutane as a main component by vaporizing the first composition in a reactor, the second composition may be added to the distillation tower to selectively recover 1,4-diaminobutane.

For example, carbonate salt of 1,4-diaminobutane may be separated into 1,4-diaminobutane and carbon dioxide, and thus 1,4-diaminobutane may be selectively recovered.

For example, the second composition including carbonate salt of 1,4-diaminobutane may be inserted into a middle region of a distillation tower, but the insertion location may be changed depending on the reaction conditions and conditions for the distillation tower.

In some embodiments of the purifying method, 1,4-diaminobutane may be recovered in a lower region of the distillation tower, and, for example, water and ions may be recovered in an upper region of the distillation tower.

According to another aspect of the present disclosure, a method of purifying 1,4-diaminobutane includes: culturing a microorganism having an ability to produce 1,4-diaminobutane in a medium while being provided with a nitrogen source to produce carbonate salt of 1,4-diaminobutane; preparing a fermented broth or a concentrate thereof that includes the carbonate salt of 1,4-diaminobutane from the medium; separating a third composition including carbonate salt of 1,4-diaminobutane by distillation of the fermented broth or a concentrate thereof; and removing carbonate from the carbonate salt of 1,4-diaminobutane in the third composition to recover 1,4-diaminobutane.

In some embodiments of the purifying method, carbonate salt of 1,4-diaminobutane may be produced by culturing a microorganism having an ability to produce 1,4-diaminobutane in a medium while being provided with a nitrogen source. That is, carbonate salt of 1,4-diaminobutane may be produced in the culturing of the microorganism.

For example, a spawn culture may be obtained by firstly culturing the microorganism having an ability to produce 1,4-diaminobutane, and then the spawn culture may be inoculated into a medium in a main culturing step to produce carbonate salt of 1,4-diaminobutane.

In particular, when a *Corynebacterium* genus microorganism is used, carbonate salt of 1,4-diaminobutane may be prepared by growing the *Corynebacterium* genus microorganism on a cornmeal malt extract agar (CMA) solid medium, inoculating the microorganism into a spawn culture medium, and then culturing the microorganism by re-inoculating the microorganism to the main culture medium.

The microorganism used in the culturing process may be any microorganism that has an ability of producing 1,4-diaminobutane which may be a microorganism that belongs to *Escherichia* sp., *Shigella* sp., *Citrobacter* sp., *Salmonella* sp., *Enterobacter* sp. *Yersinia* sp., *Klebsiella* sp., *Erwinia* sp., *Corynebacterium* sp., *Brevibacterium* sp., *Lactobacillus* sp., Selenomanas sp., *Vibrio* sp., *Pseudomonas* sp., *Streptomyces* sp., *Arcanobacterium* sp., or *Alcaligenes* sp. In some embodiments, the microorganism may belong to *Corynebacterium* sp. or *Escherichia* sp., or, for example, may be *Corynebacterium glutamicum* or *E. coli*, for example, a mutated *Corynebacterium* genus microorganism or mutated *E. coli*. For example, the microorganism having an ability of producing 1,4-diaminobutane may be mutated to enhance a biosynthetic pathway from glutamate to ornithine compared to an intrinsic activity, may be mutated to weaken activities of ornithine carbamoyltransfrase (ArgF) involved in arginine synthesis from ornithine, protein involved in discharging of glutamate, and/or protein that decomposes putrescine (or protein that is involved in acetylation) compared to the intrinsic activity, and/or may be mutated to introduce activity of ornithine decarboxylase (ODC) or to enhance the activity of ODC compared to the intrinsic activity. In particular, the microorganism may be a *Corynebacterium* KCCM11401P strain (Korean Patent No. 2014-0115244) or a *Corynebacterium* XQ37/pKKSpeC strain (Korean Patent No. 2009-0107920), but examples of the microorganism are not limited thereto.

A method of culturing the microorganism may be any known method such as batch culturing, continuous culturing, or fed-batch culturing, but examples of the method are not limited thereto, and any method available as the culturing method in the art may be used.

The culturing conditions may include introduction of oxygen or an oxygen-containing gas mixture into a culture, a culturing temperature in a range of about 20° C. to about 45° C., or, for example, about 25° C. to about 40° C. for about 10 hours to about 160 hours.

Further, a medium for the culturing used in the original culturing may include a carbon source, which may be sugar or carbohydrates (e.g.: glucose, sucrose, lactose, fructose, maltose, molasses, starch, or cellulose), oil or fat (e.g.: soybean oil, sunflower seed oil, peanut oil, and coconut oil), fatty acid (e.g., palmitic acid, stearic acid, or linoleic acid), alcohol (e.g.: glycerol and ethanol), or an organic acid (e.g.: acetic acid), but examples of the carbon source are not limited thereto, and the carbon source may be used alone or as a mixture thereof. The medium may include a phosphorus source, which may be potassium dihydrogen phosphate, potassium hydrogen phosphate, or a sodium-containing salt corresponding thereto, but examples of the phosphorus source are not limited thereto, and the phosphorus source may be used alone or as a mixture thereof. The medium may also include essential growth-promoting materials, such as other metal salts (e.g.: magnesium sulfate or iron sulfate), amino acids, or vitamins.

A material used for controlling pH and/or as a nitrogen source in the main culturing may be at least one selected from ammonia, ammonium salt of an organic compound, a nitrogen-containing organic compound, and a carbonate-based inorganic compound, but examples of the material are not limited thereto.

In particular, the material may be at least one selected from ammonia, ammonium acetate, ammonium lactate, urea, ammonium bicarbonate, and ammonium carbonate. Ammonia may be ammonia gas or ammonia water. For example, only a carbonate-based inorganic compound among the inorganic compounds may be used as the nitrogen source.

The material used for controlling pH and/or as a nitrogen source produces carbonate salt of 1,4-diaminobutane in the culture solution and prevents generation of sulfate, which separates carbonate from the carbonate salt of 1,4-diaminobutane and removed in the gaseous state during a purifying process, and thus generation of additional by-products is prevented. In this regard, the overall purifying process may be simple, and a purifying cost may decrease.

However, a sulfate-based nitrogen source, a chloride-based nitrogen source, and a nitrate-based nitrogen source such as ammonium sulfate, ammonium chloride, and ammonium nitrate are not a carbonate-based inorganic compound and thus are not included as the examples of the nitrogen source of the fermented broth. For example, a sulfate-based nitrogen source, a chloride-based nitrogen source, and a nitrate-based nitrogen source such as ammonium sulfate, ammonium chloride, and ammonium nitrate are produced as by-products, which requires additional process for their treatment, and thus the process may be complicated, and a manufacturing cost may increase.

Next, a fermented broth including carbonate salt of 1,4-diaminobutane or a concentrate thereof is prepared from the medium.

In some embodiments of the purifying method, the fermented broth may be prepared by using the resultant obtained from the culturing process as it is.

In some embodiments of the purifying method, the concentrate of the fermented broth may be prepared by concentrating the fermented broth including carbonate salt of 1,4-diaminobutane. That is, the concentrate of the fermented broth may be prepared by a process of concentrating the fermented broth.

During the concentrating of the fermented broth, at least some of a solvent included in the fermented broth may be removed. Such removal of the at least some of the solvent may increase a concentration of carbonate salt of 1,4-diaminobutane in the fermented broth. The solvent being removed may be, for example, water. In the concentrating of the fermented broth including carbonate salt of 1,4-diaminobutane, about 50% or more, or, for example, about 60% or more, about 70% or more, or about 80% or more of an initial amount of the solvent in the fermented broth before the concentrating process may be removed.

When bacterial cells are contained in the fermented broth in the concentrating of the fermented broth, the concentrating of the fermented broth may be performed in a low temperature and reduced pressure environment to prevent destruction of bacterial cells.

In some embodiments of the purifying method, the concentrating of the fermented broth may be performed at a vapor temperature of about 100° C. or lower. That is, the concentrating of the fermented broth may be performed at a temperature of about 100° C. or lower at which vapor evaporated from the fermented broth. For example, the concentrating of the fermented broth may be performed at a vapor temperature in a range of about 10° C. to about 100° C., or, for example, about 30° C. to about 80° C., or about 45° C. to about 67° C. When the vapor temperature is within these ranges, the solvent may be easily removed.

Further, the concentrating of the fermented broth may be performed at a reduced pressure of about 760 mmHg. That is, the concentrating of the fermented broth may be performed at a pressure of about 760 mmHg or lower at which a pressure of vapor is equivalent with that of the fermented broth. For example, the concentrating of the fermented broth may be performed at a pressure in a range of about 10 mmHg to about 760 mmHg, or, for example, about 40 mmHg to about 500 mmHg, or about 70 mmHg to about 200 mmHg. When the pressure is within these ranges, the solvent may be easily removed.

For example, the concentrate of the fermented broth may be performed at a vapor temperature in a range of about 10° C. to about 100° C. and a pressure in a range of about 10 mmHg to about 760 mmHg.

In the purifying method, pH of the concentrate of the fermented broth may be about 10.0 or higher. Since pH of the concentrate of the fermented broth is 10 or higher, a salt of 1,4-diaminobutane included in the fermented broth may be, for example, carbonate salt of 1,4-diaminobutane.

For example, the fermented broth may be concentrated by removing water from the fermented broth, from which bacterial cells are removed or not removed. The concentrating of the fermented broth may be omitted.

A method used for the removing of water may be a reduced-pressure concentration method and/or an evaporation method. A type of a concentrator used in the method is not particularly limited thereto, and at least one concentrator selected from a centrifugal concentrator, an evaporation concentrator, a natural circulating concentrator, a low temperature vacuum concentrator, a rotary vacuum concentrator, a vacuum evaporation concentrator, a thin film concentrator, and a planar concentrator. For example, among the concentration methods, the fermented broth may be concentrated by using a low temperature reduced pressure concentrating method.

In some embodiments, the purifying method may further include removing bacterial cells from the fermented broth or the concentrate thereof before the separating of the third composition including carbonate salt of 1,4-diaminobutane by distillation. When the bacterial cells are removed from the fermented broth or the concentrate thereof before the separating of the third composition including carbonate salt of 1,4-diaminobutane by distillation, a purity of 1,4-diaminobutane obtained by the purifying process may increase. The removed bacterial cells may be used as a byproduct, for example, as animal feed after being dried.

The removing of bacterial cells from the fermented broth may be omitted.

The removing of bacterial cells from the fermented broth may be performed using any method, for example, but not limited to, centrifugation, filter pressing, diatomite filtering, rotary vacuum filtering, membrane filtering, or coagulating/floating. For example, the removing of bacterial cells may be performed using a membrane filter. The neutral fermented broth may be separated through a membrane filter into a filtrate and bacterial cell sludgy. Bacterial cells and other impurities unable to pass through micropores of the membrane filter may be removed, while only liquid passed though the micropores of the membrane filter may be obtained as a filtrate. The residual bacterial cell sludge or bacterial cell sludge solution not included in the filtrate because of an inability to pass through the micro-pores of the membrane filter may be separated and removed from the neutral fermented broth. The membrane filter may be any filterable to remove bacterial cells from the neutral fermented broth. The operating conditions of the membrane filter to separate and remove bacterial cells from the neutral fermented broth may be easily set by one of ordinary skill in the art. For example, the neutral fermented broth may be preheated at about 50° C. before the removing of bacterial cells. This is for increasing a bacterial cells removal efficiency. When the preheating of the neutral fermented broth is performed at about 50° C., the filtrate may pass through the filter at a higher rate than at a temperature lower than 50° C., thus decreasing the filtration time, and consequently an increased productivity may also be expected. The filtration may be performed at a transmembrane pressure (TMP) of about 1.0 to 1.5 atm. The TMP is a pressure level exerted in a horizontal direction against fluid flowing in a vertical direction, i.e., a pressure exerted on the membrane by fluid) passing across the membrane filter tangentially. The pore size of the membrane filter may also be easily selected by one of ordinary skill in the art. For example, the pore size of the membrane filter may be in a range of about 0.01 µm to about 0.15 µm.

The membrane filter may have a time for gel layer formation on a surface of the membrane filter at its initial operation stage. This is for maintaining the permeate flux of the filtrate at a constant level for a long time by forming a thin layer of bacterial cells on the surface of the membrane filter. This operation may ensure a relatively constant permeate flux of the filtrate and may prevent frequent washing the membrane filter. Once the formation of the gel layer is complete, the filtrate may be obtained through the membrane filter.

In the purifying method using the fermented broth or a concentrate thereof, the carbonate salt of 1,4-diaminobutane may be at least one selected from carbonate salt of 1,4-diaminobutane ($PUT^{2+}CO_3^{2-}$, where PUT is 1,4-diaminobutane(putrescine)) and 1,4-diaminobutane bicarbonate ($PUT^{2+}(HCO_3^-)_2$).

In the purifying method using the fermented broth or a concentrate thereof, about 70 wt % or more of 1,4-diaminobutane and a salt thereof (carbonate salt of 1,4-diaminobutane) in the fermented broth or a concentrate thereof may be separated or removed by distillation. In some embodiments, about 75 wt % or more, or, for example, about 80 wt % or more, about 85 wt % or more, or about 90 wt % or more of the carbonate salt of 1,4-diaminobutane may be separated by the distillation. Also, at least a part of carbon dioxide from carbonate salt of 1,4-diaminobutane in the fermented broth or a concentrate thereof may be separated by the distillation.

In the purifying method using the fermented broth or a concentrate thereof, the separating of the third composition including carbonate salt of 1,4-diaminobutane from the fermented broth including carbonate salt of 1,4-diaminobutane or a concentrate thereof by the distillation may be performed at a vapor temperature in a range of about 30° C. to about 158° C., or, for example, about 40° C. to about 120° C. The third composition including carbonate salt of 1,4-diaminobutane may be separated with a high yield within the vapor temperature range.

In the purifying method using the fermented broth or a concentrate thereof, the separating of the third composition including carbonate salt of 1,4-diaminobutane from the fermented broth including carbonate salt of 1,4-diaminobutane or a concentrate thereof by the distillation may be performed at a pressure in a range of about 10 mmHg to about 760 mmHg, or, for example, about 70 mmHg to about 200 mmHg. The third composition including carbonate salt of 1,4-diaminobutane may be easily separated with a high yield within the pressure range.

The third composition including carbonate salt of 1,4-diaminobutane which is separated under the conditions of the temperature and the pressure described above may be obtained in a liquid state by condensation or may be used in a vapor state, not condensed, in the later steps.

In the purifying method using the fermented broth or a concentrate thereof, the third composition including carbonate salt of 1,4-diaminobutane that is separated by distillation may include carbonate salt of 1,4-diaminobutane and a solvent. For example, the third composition may only include carbonate salt of 1,4-diaminobutane and a solvent and may not include other components such as ions, amino acids, organic acids, protein, or bacterial cells.

In the separating of the third composition from the fermented broth or a concentrate thereof by distillation, an additional additive such as an alkali compound is not necessary, and by-products derived from sulfate are not generated. Therefore, the overall process becomes simple, and a cost for treating the by-products decreases, and thus the purifying method using the fermented broth or a concentrate thereof is economically advantageous.

A residual slurry resulting from the distillation process may be used as a by-product via an additional purifying process. When bacterial cells are not separated from the fermented broth, distilled water may be added to the fermented broth to completely dissolve the slurry, and then a by-product may be recovered from a parent solution after separating the bacterial cells.

In the purifying method using the fermented broth or a concentrate thereof, pH of the third composition including carbonate salt of 1,4-diaminobutane may be 10.0 or higher. Since pH of the third composition including carbonate salt of 1,4-diaminobutane obtained from the fermented broth or a concentrate thereof is 10 or higher, an additional additive such as an alkali compound is not necessary to increase pH of the third composition.

The third composition including carbonate salt of 1,4-diaminobutane obtained by distillation may include 1,4-diaminobutane bicarbonate and/or 1,4-diaminobutane carbonate. For example, the third composition including carbonate salt of 1,4-diaminobutane may include 1,4-diaminobutane bicarbonate as a main component or may include 1,4-diaminobutane carbonate as a main component. For example, the third composition including carbonate salt of 1,4-diaminobutane may include only 1,4-diaminobutane bicarbonate or may include only 1,4-diaminobutane carbonate in addition to a solvent.

In the purifying method using the fermented broth or a concentrate thereof, the third composition including carbonate salt of 1,4-diaminobutane may be in a gaseous state, a liquid state, or a mixed state thereof. A state of the third composition including carbonate salt of 1,4-diaminobutane may vary depending on required purifying conditions.

In some embodiments, vapor and/or condensate of the third composition including carbonate salt of 1,4-diaminobutane obtained by distillation in the separation process may be recovered. The separating of the third composition by distillation may be performed using a double jacketed reactor.

The removing of carbonic acid from the carbonate salt of 1,4-diaminobutane in the third composition to recover 1,4-diaminobutane may be performed by fractional distillation.

Due to the recovering of 1,4-diaminobutane from the third composition including carbonate salt of 1,4-diaminobutane by fractional distillation, carbon dioxide may be separated from carbonate salt of 1,4-diaminobutane, and 1,4-diaminobutane may be recovered.

For example, the third composition including carbonate salt of 1,4-diaminobutane may be separated from the fermented broth or a concentrate thereof by distillation, condensed, and stored. Then, the separated composition may be used in the recovering of 1,4-diaminobutane.

The third composition including carbonate salt of 1,4-diaminobutane may be stored in a reservoir disposed between a top of the reactor and a distillation column, but not limited thereto, and any storing method in the art may be used.

In some embodiments of the purifying method, the separating of the third composition including carbonate salt of 1,4-diaminobutane by distillation and the recovering of 1,4-diaminobutane by fractional distillation may be continuously performed. In other words, the third composition including carbonate salt of 1,4-diaminobutane may be separated from the fermented broth or a concentrate thereof by distillation and at the same time the composition may be further separated into 1,4-diaminobutane and carbonic acid by fractional distillation to recover 1,4-diaminobutane. The 1,4-diaminobutane recovered by fractional distillation may be a final product.

In some embodiments of the purifying method, the fractional distillation may be operated at a vapor temperature in a range of about 100° C. to about 230° C. and a pressure of room pressure of higher, i.e., in a range of about 1 atm to about 5 atm, or, for example, at a vapor temperature in a range of 100° C. to about 158° C. and room pressure. The 1,4-diaminobutane may be obtained with a high yield within these temperature and pressure ranges.

In some embodiments of the purifying method, the recovering of 1,4-diaminobutane may be performed using a distillation tower. For example, after preparing the third composition including carbonate salt of 1,4-diaminobutane as a main component by vaporizing the fermented broth or a concentrate thereof in a reactor, the third composition may be added to the distillation tower to selectively recover 1,4-diaminobutane. For example, the carbonate salt of 1,4-diaminobutane may be separated into 1,4-diaminobutane and carbon dioxide, and thus 1,4-diaminobutane may be selectively recovered. For example, the third composition including carbonate salt of 1,4-diaminobutane may be inserted into a middle region of the distillation tower, but the insertion location may change depending on the reaction conditions and conditions for the distillation tower.

In some embodiments of the purifying method, 1,4-diaminobutane may be recovered in a lower region of the distillation tower, and, for example, water and ions may be recovered in an upper region of the distillation tower.

1,4-diaminobutane refined by a method according to one of the above-described embodiments may have a recovery ratio of about 60 wt % or greater, and in some embodiments, about 65 wt % or greater, and in some other embodiments, about 75 wt % or greater, and in still other embodiments, about 85 wt % or greater, and in yet other embodiments, about 90.0 wt % or greater.

Furthermore, 1,4-diaminobutane refined by a method according to one of the above-described embodiments may have a purity of about 90.0 wt % or higher and a recovery ratio of about 90.0 wt %. In some embodiments, the 1,4-diaminobutane may have a purity of about 91.0 wt % or higher and a recovery ratio of about 91.0 wt % or greater, and in some other embodiments, a purity of about 92.0 wt % or higher and a recovery ratio of about 92.0 wt %. These purities of 1,4-diaminobutane denotes amounts of 1,4-diaminobutane in a mixture of water and 1,4-diaminobutane obtained in a lower region of the distillation column.

MODE OF THE INVENTION

Hereinafter, one or more embodiments of the present disclosure will now be described in detail with reference to the following examples. However, these examples are only for illustrative purposes and are not intended to limit the scope of the one or more embodiments of the present disclosure.

Purifying of 1,4-Diaminobutane

Example 1: 1,4-Diaminobutane Purifying Method Using NH3 without Removing Bacterial Cells (Fermentation Step)

1) Spawn Culture: Spawn Culture of Bacteria Producing 1,4-Diaminobutane 400 mL of a medium containing 30.0 g/L of glucose, 15 g/L of molasses, 1.11 g/L of phosphoric acid, 5.8 g/L of magnesium sulfate 7 hydrate, 10.0 g/L of corn steep liquor, 0.5 g/L of arginine, 1.0 mg/L of biotin, 20.0 mg/L of thiamine pyrophosphate, 20.0 mg/L of calcium pathothenate, 20.0 mg/L of nicotinic acid, and 0.2 g/L of anti-foaming agent was added to a 1 L-glass fermenter and heated to main a temperature of 120° C. for 20 minutes to perform sterilization.

The sterilized fermenter was cooled to a temperature of 30° C., bacterial cells, i.e., *Corynebacterium* KCCM11401P (Korean Patent No. 2014-0115244) pre-grown on a cornmeal malt extract agar (CMA) solid medium for 12 hours were inoculated into the medium, and the bacterial cells were cultured with sufficient air circulation and stirring process at 30° C. to obtain a spawn culture. In the spawn culturing, ammonium gas was provided as a pH control and a nitrogen source.

2) Main Culture 1500 mL of a medium containing 120.0 g/L of glucose, 7.0 g/L of molasses, 0.7 g/L of phosphoric acid, 2.0 g/L of magnesium sulfate 7 hydrate, 5.0 g/L of corn steep liquor, 0.5 g/L of arginine, 1.0 mg/L of biotin, 20.0 mg/L of thiamine pyrophosphate, 20.0 mg/L of calcium pathothenate, 20.0 mg/L of nicotinic acid, and 0.3 g/L of anti-foaming agent was added to a 5 L-glass fermenter and heated to main a temperature of 120° C. for 20 minutes to perform sterilization.

The sterilized fermenter was cooled to a temperature of 30° C. to prepare a spawn culture, and 370 ml of the spawn culture was inoculated into the medium prepared as described above, and bacterial cells therein were cultured with sufficient air circulation and stirring process at 30° C. Ammonium gas was provided as a nitrogen source, and the ammonium gas was provided not to exhaust the nitrogen source of the culture, and thus pH of the culture was controlled.

As a result of the culturing, 31.2 g/L of 1,4-diaminobutane was accumulated in the fermented broth, and pH of the fermented broth was 8.0.

(Concentration Step)

6,700 g of the fermented broth including 1,4-diaminobutane bicarbonate was added to a 10 L-concentrator (available from Eylela, Tokyo, Japan). While a vapor temperature and a pressure were maintained at 47° C. and 80 mmHg, 79.5% of the fermented broth was removed to prepare a concentrate. Here, the removed condensate was 5,327 g, and 1,4-diaminobutane was not detected from the removed condensate. Table 1 is a component analysis table before and after the concentration step. 1,4-diaminobutane, amino acid, organic acid, protein, and ions in Table 1 were analyzed by using HPLC, and water was analyzed by using a Karl-fischer method of water analysis.

TABLE 1

| Component | Fermented broth (g) | Condensate after concentration (g) | Concentrate (g) |
|---|---|---|---|
| pH | 8.0 | 7.1 | 10.5 |
| Water | 6,142.6 | 5,187.2 | 960.0 |
| 1,4-Diaminobutane | 0.0 | 0.0 | 0.0 |
| 1,4-Diaminobutane bicarbonate | 489.3 | 0.0 | 0.0 |
| 1,4-Diaminobutane carbonate | 0.0 | 0.0 | 344.8 |
| Ions | 7.4 | 139.8 | 7.4 |
| Amino acid | 5.5 | 0.0 | 5.5 |
| Organic acid | 6.1 | 0.0 | 6.1 |
| Protein | 1.5 | 0.0 | 1.5 |
| Bacterial cells | 47.7 | 0.0 | 47.7 |
| Total | 6,700.0 | 5,327.0 | 1,373.0 |

(Distillation Step)

1,373 g of the prepared concentrate was added to a 5 L-double jacket reactor. The double jacket reactor is equipped with an upper condenser, a condensate device, and a device for pressure control. The double jacket reactor distilled the concentrate at a vapor temperature in a range of about 50° C. to about 95° C. and a pressure of about 80 mmHg. In the initial stage, a vapor temperature in the double jacket reactor was maintained at 47° C. due to water evaporation, but as 1,4-diaminobutane evaporated, the vapor temperature increased up to 95° C. The evaporated vapor was condensed in the condensate device via the condensate device. An amount of the condensate was 1,286.4 g, and an amount of the residue after the evaporation was 86.6 g. Table 2 is a component analysis table before and after the distillation.

TABLE 2

| Component | Concentrate (g) | Residue after evaporation (g) | Condensate (g) |
|---|---|---|---|
| pH | 10.5 | — | 11.1 |
| Water | 960.0 | 0.0 | 960.0 |
| 1,4-Diaminobutane | 0.0 | 18.5 | 0.0 |
| 1,4-Diaminobutane bicarbonate | 0.0 | 0.0 | 0.0 |
| 1,4-Diaminobutane carbonate | 344.8 | 0.0 | 326.4 |
| Ions | 7.4 | 7.4 | 0.0 |
| Amino acid | 5.5 | 5.5 | 0.0 |
| Organic acid | 6.1 | 6.1 | 0.0 |
| Protein | 1.5 | 1.5 | 0.0 |
| Bacterial cells | 47.7 | 47.7 | 0.0 |
| Total | 1,373.0 | 86.6 | 1,286.4 |

(Fractional Distillation Step)

1,286.4 g of the condensate including 1,4-diaminobutane was added to a distillation column having 20 stages (available from Ace Glass Incorporate, USA). 1,086.3 g of water and carbonate were recovered at an upper region of the distillation column, and 200.1 g of 1,4-diaminobutane was recovered at a lower region of the distillation column (an amount of the resultant estimated by HPLC was 92.8%). A recovery ratio of 1,4-diaminobutane was about 90.6 wt %.

From the distillation column, carbonate of carbonate salt of 1,4-diaminobutane was separated at a vapor temperature in a range of about 100° C. to about 158° C. and room pressure, and thus 1,4-diaminobutane was recovered. Table 3 is a component analysis table before and after a decarboxylation step.

TABLE 3

| Component | Evaporated condensate (g) | Upper region of distillation column (g) | Lower region of distillation column (g) |
|---|---|---|---|
| pH | 11.1 | 7.3 | 13.5 |
| Water | 960.0 | 945.6 | 14.4 |
| 1,4-Diaminobutane | 0.0 | 0.9 | 185.7 |
| 1,4-Diaminobutane bicarbonate | 0.0 | 0.0 | 0.0 |
| 1,4-Diaminobutane carbonate | 326.4 | 0.0 | 0.0 |
| Ions | 0.0 | 139.8 | 0.0 |
| Amino acid | 0.0 | 0.0 | 0.0 |
| Organic acid | 0.0 | 0.0 | 0.0 |
| Protein | 0.0 | 0.0 | 0.0 |
| Bacterial cells | 0.0 | 0.0 | 0.0 |
| Total | 1,286.4 | 1,086.3 | 200.1 |

Example 2: 1,4-Diaminobutane Purifying Method Using NH3 after Removing Bacterial Cells (Fermentation Step)

A fermented broth was prepared by performing a spawn culture and a main culture in the same manner as in Example 1.

(Bacterial Cells Separation Step)

13,400 g of the fermented broth was added to a 15 L-basket, and the fermented broth was filtered by using a membrane filter (Pellicon 2, a pore size: 0.1 μm, a membrane area: 0.5 m², available from Milipore) in the form of a cartridge.

The fermented broth was added to the membrane filter, 400.0 g of a sludge of bacterial cells was separated and removed under conditions including a temperature of 60° C. and a transmembrane pressure (TMP) of 1.2 atm, and an amount of the filtrate thus obtained was 13,000 g. Table 4 is a component analysis table before and after separating bacterial cells.

TABLE 4

| Component | Fermented broth (g) | Sludge of bacterial cells (g) | Filtrate (g) |
|---|---|---|---|
| pH | 8.0 | 8.0 | 8.0 |
| Water | 12,285.1 | 293.6 | 11,991.6 |
| 1,4-Diaminobutane | 0.0 | 0.0 | 0.0 |
| 1,4-Diaminobutane bicarbonate | 978.6 | 10.7 | 967.9 |

TABLE 4-continued

| Component | Fermented broth (g) | Sludge of bacterial cells (g) | Filtrate (g) |
|---|---|---|---|
| 1,4-Diaminobutane carbonate | 0.0 | 0.0 | 0.0 |
| Ions | 14.9 | 0.2 | 14.7 |
| Amino acid | 10.9 | 0.1 | 10.8 |
| Organic acid | 12.2 | 0.1 | 12.0 |
| Protein | 3.0 | 0.0 | 3.0 |
| Bacterial cells | 95.3 | 95.3 | 0.0 |
| Total | 13,400.0 | 400.0 | 13,000.0 |

(Concentration Step)

A concentration step was performed in the same manner as in Example 1, except that the filtrate was used. 6,500 g of the filtrate was added, and 82.5% of the fermented broth was removed to perform the concentration. An amount of the removed condensate was 5.365 g, and 1,4-diaminobutane was not detected from the removed condensate. Table 5 is a component analysis table before and after the concentration step.

TABLE 5

| Component | Filtrate (g) | Condensate after concentration (g) | Concentrate (g) |
|---|---|---|---|
| pH | 8.0 | 7.0 | 10.7 |
| Water | 5,995.8 | 5,226.7 | 773.7 |
| 1,4-Diaminobutane | 0.0 | 0.0 | 0.0 |
| 1,4-Diaminobutane bicarbonate | 484.0 | 0.0 | 0.0 |
| 1,4-Diaminobutane carbonate | 0.0 | 0.0 | 341.1 |
| Ions | 7.3 | 138.3 | 7.3 |
| Amino acid | 5.4 | 0.0 | 5.4 |
| Organic acid | 6.0 | 0.0 | 6.0 |
| Protein | 1.5 | 0.0 | 1.5 |
| Bacterial cells | 0.0 | 0.0 | 0.0 |
| Total | 6,500 | 5,365.0 | 1,135.0 |

(Distillation Step)

A distillation step was performed in the same manner as in Example 1, except that the concentrate was used. 1,135 g of the concentrate was added to obtain 1,101.8 g of the condensate and 33.2 g of the residue. Table 6 is a component analysis table before and after the distillation step.

TABLE 6

| Component | Concentrate (g) | Residue after evaporation (g) | Evaporated condensate (g) |
|---|---|---|---|
| pH | 10.7 | — | 11.3 |
| Water | 773.7 | 0.0 | 773.7 |
| 1,4-Diaminobutane | 0.0 | 13.0 | 0.0 |
| 1,4-Diaminobutane bicarbonate | 0.0 | 0.0 | 0.0 |
| 1,4-Diaminobutane carbonate | 341.1 | 0.0 | 328.1 |
| Ions | 7.3 | 7.3 | 0.0 |
| Amino acid | 5.4 | 5.4 | 0.0 |
| Organic acid | 6.0 | 6.0 | 0.0 |
| Protein | 1.5 | 1.5 | 0.0 |
| Bacterial cells | 0.0 | 0.0 | 0.0 |
| Total | 1,135.0 | 33.2 | 1,101.8 |

(Fractional Distillation Step)

A fractional distillation step was performed in the same manner as in Example 1, except that the condensate was used. 1,101.8 g of the condensate was added to the distillation column. 902.3 g of the resultant was recovered at an upper region of the distillation column, and 199.5 g of the resultant was recovered at a lower region of the distillation column (an amount of the resultant estimated by HPLC was 91.8%). A recovery ratio of 1,4-diaminobutane was about 91.8 wt %. Table 7 is a component analysis table before and after the decarboxylation step.

TABLE 7

| Component | Evaporated condensate (g) | Upper region of distillation column (g) | Lower region of distillation column (g) |
|---|---|---|---|
| pH | 11.3 | 7.1 | 13.3 |
| Water | 773.7 | 762.5 | 11.2 |
| 1,4-Diaminobutane | 0.0 | 1.5 | 188.3 |
| 1,4-Diaminobutane bicarbonate | 0.0 | 0.0 | 0.0 |
| 1,4-Diaminobutane carbonate | 328.1 | 0.0 | 0.0 |
| Ions | 0.0 | 138.3 | 0.0 |
| Amino acid | 0.0 | 0.0 | 0.0 |
| Organic acid | 0.0 | 0.0 | 0.0 |
| Protein | 0.0 | 0.0 | 0.0 |
| Bacterial cells | 0.0 | 0.0 | 0.0 |
| Total | 1,101.8 | 902.3 | 199.5 |

Example 3: 1,4-Diaminobutane Purifying Method Using NH3 without Concentration after Removing Bacterial Cells (Fermentation Step)

A fermented broth was prepared by performing a spawn culture and a main culture in the same manner as in Example 1.

(Bacterial Cells Separation Step)

A bacterial cells separation step was performed in the same manner as in Example 2.

(Distillation Step)

A distillation step was performed in the same manner as in Example 1, except that the filtrate, from which bacterial cells were separated, was used. 6,500 g of the filtrate was added to obtain 6,465.7 g of the condensate and 34.3 g of the residue. Table 8 is a component analysis table before and after the distillation step.

TABLE 8

| Component | Concentrate (g) | Residue after evaporation (g) | Evaporated condensate (g) |
|---|---|---|---|
| pH | 8.0 | — | 10.8 |
| Water | 5,995.8 | 14.0 | 6,000.3 |
| 1,4-Diaminobutane | 0.0 | 7.3 | 0.0 |
| 1,4-Diaminobutane bicarbonate | 484.0 | 0.0 | 465.4 |
| 1,4-Diaminobutane carbonate | 0.0 | 0.0 | 0.0 |
| Ions | 7.3 | 0.0 | 0.0 |
| Amino acid | 5.4 | 5.4 | 0.0 |
| Organic acid | 6.0 | 6.0 | 0.0 |
| Protein | 1.5 | 1.5 | 0.0 |
| Bacterial cells | 0.0 | 0.0 | 0.0 |
| Total | 6,500 | 34.3 | 6,465.7 |

(Fractional Distillation Step)

A fractional distillation step was performed in the same manner as in Example 1, except that the condensate was used. 6,465.7 g of the condensate was added to the distillation column. 6,266.3 g of the resultant was recovered at an upper region of the distillation column, and 199.4 g of the resultant was recovered at a lower region of the distillation column (an amount of the resultant estimated by HPLC was 94.1%). A recovery ratio of 1,4-diaminobutane was about 91.5 wt %. Table 9 is a component analysis table before and after the decarboxylation step.

TABLE 9

| Component | Evaporated condensate (g) | Upper region of distillation column (g) | Lower region of distillation column (g) |
|---|---|---|---|
| pH | 10.8 | 6.9 | 13.4 |
| Water | 6,000.3 | 5,988.6 | 11.8 |
| 1,4-Diaminobutane | 0.0 | 1.2 | 187.7 |
| 1,4-Diaminobutane bicarbonate | 465.4 | 0.0 | 0.0 |
| 1,4-Diaminobutane carbonate | 0.0 | 0.0 | 0.0 |
| Ions | 0.0 | 276.5 | 0.0 |
| Amino acid | 0.0 | 0.0 | 0.0 |
| Organic acid | 0.0 | 0.0 | 0.0 |
| Protein | 0.0 | 0.0 | 0.0 |
| Bacterial cells | 0.0 | 0.0 | 0.0 |
| Total | 6,465.7 | 6,266.3 | 199.4 |

Example 4: 1,4-Diaminobutane Purifying Method Using Ammonium Acetate without Removing Bacterial Cells (Fermentation Step)

1) Spawn culture: Spawn culture of bacteria producing 1,4-diaminobutane

A spawn culture was performed in the same manner as in Example 1.

2) Main Culture

A main culture was performed in the same manner as in Example 1, except that ammonium acetate was used instead of ammonia gas, as a nitrogen source.

The culture was performed while dropwisely adding 100 mL of 600 g/L ammonium acetate, as a nitrogen source.

As a result of the culture, 30.6 g/L of 1,4-diaminobutane was accumulated in the fermented broth, and pH of the fermented broth was 8.0.

(Concentration Step)

A concentration step was performed in the same manner as in Example 1, except that the fermented broth was used.

6,700 g of the fermented broth was added, and 81.6% of the fermented broth was removed to prepare a concentrate. Here, an amount of the removed condensate was 5,461 g, and 1,4-diaminobutane was not detected from the removed condensate. Table 10 is a component analysis table before and after the concentration step.

TABLE 10

| Component | Filtrate (g) | Condensate after concentration (g) | Concentrate (g) |
|---|---|---|---|
| pH | 8.0 | 7.3 | 10.6 |
| Water | 6,100.9 | 5,307.2 | 798.8 |
| 1,4-Diaminobutane | 0.0 | 0.0 | 0.0 |
| 1,4-Diaminobutane bicarbonate | 514.0 | 0.0 | 0.0 |
| 1,4-Diaminobutane carbonate | 0.0 | 0.0 | 355.0 |
| Ions | 9.5 | 153.8 | 9.5 |
| Amino acid | 6.5 | 0.0 | 6.5 |
| Organic acid | 6.0 | 0.0 | 6.0 |
| Protein | 4.8 | 0.0 | 4.8 |
| Bacterial cells | 58.3 | 0.0 | 58.3 |
| Total | 6,700.0 | 5,461.0 | 1,239.0 |

(Distillation Step)

A distillation step was performed in the same manner as in Example 1, except that the concentrate was used.

1,239 g of the concentrate was added to obtain 1,135.4 g of the condensate and 103.6 g of the residue. Table 11 is a component analysis table before and after the distillation step.

TABLE 11

| Component | Concentrate (g) | Residue after evaporation (g) | Evaporated condensate (g) |
|---|---|---|---|
| pH | 10.6 | — | 11.4 |
| Water | 798.8 | 0.0 | 798.8 |
| 1,4-Diaminobutane | 0.0 | 18.5 | 0.0 |
| 1,4-Diaminobutane bicarbonate | 0.0 | 0.0 | 0.0 |
| 1,4-Diaminobutane carbonate | 355.0 | 0.0 | 366.6 |
| Ions | 9.5 | 9.5 | 0.0 |
| Amino acid | 6.5 | 6.5 | 0.0 |
| Organic acid | 6.0 | 6.0 | 0.0 |
| Protein | 4.8 | 4.8 | 0.0 |
| Bacterial cells | 58.3 | 58.3 | 0.0 |
| Total | 1,239.0 | 103.6 | 1,135.4 |

(Fractional Distillation Step)

A fractional distillation step was performed in the same manner as in Example 1, except that the condensate was used. 1,135.4 g of the condensate was added to the distillation column. 943.8 g of the resultant was recovered at an upper region of the distillation column, and 191.5 g of the resultant was recovered at a lower region of the distillation column (an amount of the resultant estimated by HPLC was 94.9%). A recovery ratio of 1,4-diaminobutane was about 90.3 wt %. Table 12 is a component analysis table before and after the decarboxylation step.

TABLE 12

| Component | Evaporated condensate (g) | Upper region of distillation column (g) | Lower region of distillation column (g) |
|---|---|---|---|
| pH | 11.4 | 7.3 | 13.5 |
| Water | 798.8 | 789.1 | 9.8 |
| 1,4-Diaminobutane | 0.0 | 0.9 | 181.7 |
| 1,4-Diaminobutane bicarbonate | 0.0 | 0.0 | 0.0 |
| 1,4-Diaminobutane carbonate | 366.6 | 0.0 | 0.0 |
| Ions | 0.0 | 153.8 | 0.0 |

TABLE 12-continued

| Component | Evaporated condensate (g) | Upper region of distillation column (g) | Lower region of distillation column (g) |
|---|---|---|---|
| Amino acid | 0.0 | 0.0 | 0.0 |
| Organic acid | 0.0 | 0.0 | 0.0 |
| Protein | 0.0 | 0.0 | 0.0 |
| Bacterial cells | 0.0 | 0.0 | 0.0 |
| Total | 1,135.4 | 943.8 | 191.5 |

Example 5: 1,4-Diaminobutane Purifying Method Using Ammonium Acetate after Removing Bacterial Cells (Fermentation Step)
A fermented broth was prepared by performing a spawn culture and a main culture in the same manner as in Example 4.

(Bacterial Cells Separation Step)
A bacterial cells separation step was performed in the same manner as in Example 2.

13,400 g of the fermented broth was added to separate and remove 400.0 g of a sludge of bacterial cells, and thus 13,000 g of the filtrate was obtained. Table 13 is a component analysis table before and after separating the bacterial cells.

TABLE 13

| Component | Fermented broth (g) | Sludge of bacterial cells (g) | Filtrate (g) |
|---|---|---|---|
| pH | 8.0 | 8.0 | 8.0 |
| Water | 12,201.7 | 271.1 | 11,930.6 |
| 1,4-Diaminobutane | 0.0 | 0.0 | 0.0 |
| 1,4-Diaminobutane bicarbonate | 1,028.0 | 11.7 | 1,016.3 |
| 1,4-Diaminobutane carbonate | 0.0 | 0.0 | 0.0 |
| Ions | 19.0 | 0.2 | 18.8 |
| Amino acid | 13.1 | 0.1 | 12.9 |
| Organic acid | 12.0 | 0.1 | 11.8 |
| Protein | 9.6 | 0.1 | 9.5 |
| Bacterial cells | 116.6 | 116.6 | 0.0 |
| Total | 13,400.0 | 400.0 | 13,000.0 |

(Concentration Step)
A concentration step was performed in the same manner as in Example 1, except that the filtrate was used. 6,500 g of the filtrate was added, and 83.4% of the fermented broth (filtrate) was removed. Here, an amount of the removed condensate was 5,421 g, and 1,4-diaminobutane was not detected from the removed condensate. Table 14 is a component analysis table before and after the concentration step.

TABLE 14

| Component | Filtrate (g) | Condensate after concentration (g) | Concentrate (g) |
|---|---|---|---|
| pH | 8.0 | 7.1 | 10.8 |
| Water | 5,965.3 | 5,268.9 | 701.5 |
| 1,4-Diaminobutane | 0.0 | 0.0 | 0.0 |
| 1,4-Diaminobutane bicarbonate | 508.1 | 0.0 | 351.0 |
| 1,4-Diaminobutane carbonate | 0.0 | 0.0 | 0.0 |
| Ions | 9.4 | 152.1 | 9.4 |
| Amino acid | 6.5 | 0.0 | 6.5 |
| Organic acid | 5.9 | 0.0 | 5.9 |
| Protein | 4.8 | 0.0 | 4.8 |
| Bacterial cells | 0.0 | 0.0 | 0.0 |
| Total | 6,500.0 | 5,421.0 | 1,079.0 |

(Distillation Step)
A distillation step was performed in the same manner as in Example 1, except that the concentrate was used. 1,079 g of the concentrate was added to obtain 1,041.1 g of the condensate and 37.9 g of the residue. Table 15 is a component analysis table before and after the distillation step.

TABLE 15

| Component | Concentrate (g) | Residue after evaporation (g) | Evaporated condensate (g) |
|---|---|---|---|
| pH | 10.8 | — | 11.3 |
| Water | 701.5 | 0.0 | 701.5 |
| 1,4-Diaminobutane | 0.0 | 11.3 | 0.0 |
| 1,4-Diaminobutane bicarbonate | 351.0 | 0.0 | 0.0 |
| 1,4-Diaminobutane carbonate | 0.0 | 0.0 | 339.6 |
| Ions | 9.4 | 9.4 | 0.0 |
| Amino acid | 6.5 | 6.5 | 0.0 |
| Organic acid | 5.9 | 5.9 | 0.0 |
| Protein | 4.8 | 4.8 | 0.0 |
| Bacterial cells | 0.0 | 0.0 | 0.0 |
| Total | 1,079.0 | 37.9 | 1,041.1 |

(Fractional Distillation Step)
A fractional distillation step was performed in the same manner as in Example 1, except that the condensate was used. 1,041.1 g of the condensate was added to the distillation column. 847.4 g of the resultant was recovered at an upper region of the distillation column, and 193.8 g of the resultant was recovered at a lower region of the distillation column (an amount of the resultant estimated by HPLC was 96.2%). A recovery ratio of 1,4-diaminobutane was about 92.6 wt %. Table 16 is a component analysis table before and after the decarboxylation step.

TABLE 16

| Component | Evaporated condensate (g) | Upper region of distillation column (g) | Lower region of distillation column (g) |
|---|---|---|---|
| pH | 11.3 | 7.2 | 13.5 |
| Water | 701.5 | 694.1 | 7.4 |
| 1,4-Diaminobutane | 0.0 | 1.2 | 186.4 |
| 1,4-Diaminobutane bicarbonate | 0.0 | 0.0 | 0.0 |
| 1,4-Diaminobutane carbonate | 339.6 | 0.0 | 0.0 |
| Ions | 0.0 | 152.1 | 0.0 |
| Amino acid | 0.0 | 0.0 | 0.0 |
| Organic acid | 0.0 | 0.0 | 0.0 |
| Protein | 0.0 | 0.0 | 0.0 |
| Bacterial cells | 0.0 | 0.0 | 0.0 |
| Total | 1,041.1 | 847.4 | 193.8 |

Example 6: 1,4-Diaminobutane Purifying Method Using Ammonium Acetate after Removing Bacterial Cells without Concentration (Fermentation Step)

A was prepared by performing a spawn culture and a main culture in the same manner as in Example 4.

(Bacterial Cells Separation Step)

A bacterial cells separation step was performed in the same manner as in Example 5.

(Distillation Step)

A distillation step was performed in the same manner as in Example 1, except that the filtrate was used. 6,500 g of the filtrate was added to obtain 6,459.3 g of the condensate and 40.7 g of the residue. Table 17 is a component analysis table before and after the distillation step.

TABLE 17

| Component | Concentrate (g) | Residue after evaporation (g) | Evaporated condensate (g) |
|---|---|---|---|
| pH | 8.0 | — | 10.9 |
| Water | 5,965.3 | 0.0 | 5,970.4 |
| 1,4-Diaminobutane | 0.0 | 14.1 | 0.0 |
| 1,4-Diaminobutane bicarbonate | 508.1 | 0.0 | 0.0 |
| 1,4-Diaminobutane carbonate | 0.0 | 0.0 | 489.0 |
| Ions | 9.4 | 9.4 | 0.0 |
| Amino acid | 6.5 | 6.5 | 0.0 |
| Organic acid | 5.9 | 5.9 | 0.0 |
| Protein | 4.8 | 4.8 | 0.0 |
| Bacterial cells | 0.0 | 0.0 | 0.0 |
| Total | 6,500.0 | 40.7 | 6,459.3 |

(Fractional Distillation Step)

A fractional distillation step was performed in the same manner as in Example 1, except that the condensate was used. 6,459.3 g of the condensate was added to the distillation column. 6,268.5 g of the resultant was collected at an upper region of the distillation column, and 190.8 g of the resultant was recovered at a lower region of the distillation column (an amount of the resultant estimated by HPLC was 96.5%). A recovery ratio of 1,4-diaminobutane was about 91.5 wt %. Table 18 is a component analysis table before and after the decarboxylation step.

TABLE 18

| Component | Evaporated condensate (g) | Upper region of distillation column (g) | Lower region of distillation column (g) |
|---|---|---|---|
| pH | 10.9 | 7.1 | 13.4 |
| Water | 5,970.4 | 5,963.7 | 6.7 |
| 1,4-Diaminobutane | 0.0 | 0.6 | 184.1 |
| 1,4-Diaminobutane bicarbonate | 0.0 | 0.0 | 0.0 |
| 1,4-Diaminobutane carbonate | 489.0 | 0.0 | 0.0 |
| Ions | 0.0 | 304.2 | 0.0 |
| Amino acid | 0.0 | 0.0 | 0.0 |
| Organic acid | 0.0 | 0.0 | 0.0 |
| Protein | 0.0 | 0.0 | 0.0 |
| Bacterial cells | 0.0 | 0.0 | 0.0 |
| Total | 6,459.3 | 6,268.5 | 190.8 |

Comparative Example 1: 1,4-Diaminobutane Purifying Method Using Ammonium Sulfate after Removing Bacterial Cells (Fermentation Step)

1) Spawn Culture: Spawn Culture of Bacteria Producing 1,4-Diaminobutane

A spawn culture was performed in the same manner as in Example 1, except that ammonia was used to control pH, and 5.0 g/L of ammonium sulfate was used instead of ammonia, as a nitrogen source.

2) Main Culture

A main culture was performed in the same manner as in Example 1, except that 50.0 g/L of ammonium sulfate was used instead of ammonia gas, as a nitrogen source.

As a result of the culturing, 30.1 g/L of 1,4-diaminobutane was accumulated in the fermented broth, and pH of the fermented broth was 7.1.

(Bacterial Cells Separation Step)

A bacterial cells separation step was performed in the same manner as in Example 2.

13,400 g of the fermented broth was added to separate and remove 400.0 g of a sludge of bacterial cells, and thus 13,000 g of the filtrate was obtained. Table 19 is a component analysis table before and after separating the bacterial cells.

TABLE 19

| Component | Fermented broth (g) | Sludge of bacterial cells (g) | Filtrate (g) |
|---|---|---|---|
| pH | 7.1 | 7.1 | 7.1 |
| Water | 12,437.3 | 298.5 | 12,138.8 |
| 1,4-Diaminobutane | 396.4 | 5.1 | 391.3 |
| Ions | 450.4 | 0.2 | 444.6 |
| Amino acid | 11.0 | 0.1 | 10.8 |
| Organic acid | 11.8 | 0.2 | 11.6 |
| Protein | 2.9 | 0.0 | 2.9 |
| Bacterial cells | 90.3 | 90.3 | 0.0 |
| Total | 13,400.0 | 400.0 | 13,000.0 |

(Concentration Step)

A concentration step was performed in the same manner as in Example 1, except that the filtrate was used.

6,500 g of the filtrate was added, and 82.3% of the fermented broth (filtrate) was removed to prepare a concentrate. Here, an amount of the removed condensate was 5,350 g, and 1,4-diaminobutane was not detected from the removed condensate. Table 20 is a component analysis table before and after the concentration step.

TABLE 20

| Component | Filtrate (g) | Condensate after concentration (g) | Concentrate (g) |
|---|---|---|---|
| pH | 7.1 | 8.0 | 6.8 |
| Water | 6,069.4 | 5,350.0 | 719.4 |
| 1,4-diaminobutane | 195.7 | 0.0 | 195.7 |
| Ions | 222.3 | 0.0 | 222.3 |
| Amino acid | 5.4 | 0.0 | 5.4 |
| Organic acid | 5.8 | 0.0 | 5.8 |
| Protein | 1.4 | 0.0 | 1.4 |
| Bacterial cells | 0.0 | 0.0 | 0.0 |
| Total | 6,500.0 | 5,350.0 | 1,150.0 |

(Distillation Step)

A distillation step was performed in the same manner as in Example 1, except that the concentrate was used.

1,150 g of the concentrate was added to obtain 719.4 g of the condensate and 430.6 g of the residue. 1,4-diaminobutane was precipitated as sulfuric acid salt crystals of 1,4-diaminobutane and thus was not recovered as a condensate. Table 21 is a component analysis table before and after the distillation step.

TABLE 21

| Component | Concentrate (g) | Residue after evaporation (g) | Evaporated condensate (g) |
|---|---|---|---|
| pH | 6.8 | — | 7.3 |
| Water | 719.4 | 0.0 | 719.4 |
| 1,4-diaminobutane | 195.7 | 195.7 | 0.0 |
| Ions | 222.3 | 222.3 | 0.0 |
| Amino acid | 5.4 | 5.4 | 0.0 |
| Organic acid | 5.8 | 5.8 | 0.0 |
| Protein | 1.4 | 1.4 | 0.0 |
| Bacterial cells | 0.0 | 0.0 | 0.0 |
| Total | 1,150.0 | 430.6 | 719.4 |

INDUSTRIAL APPLICABILITY

When the purifying method according to one or more embodiments of the present disclosure is used, 1,4-diaminobutane may be easily obtained with a high yield from a composition including carbonate salt of 1,4-diaminobutane. Furthermore, since consumption of an alkali compound required in the purifying method is reduced along with a reduction in an amount of by-products, which generated an additional cost, a cost for the purifying method thus used may be decreased as well It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the inventive concept as defined by the following claims.

Industrial Applicability

The invention claimed is:

1. A method for purifying 1,4-diaminobutane comprising the steps of:
    separating a second composition comprising carbonate salt of 1,4-diaminobutane from a first composition comprising carbonate salt of 1,4-diaminobutane by distillation; and
    removing carbonate from the carbonate salt of 1,4-diaminobutane comprised in the second composition to recover 1,4-diaminobutane.

2. The method according to claim 1, wherein the carbonate salt of 1,4-diaminobutane is at least one of 1,4-diaminobutane carbonate and 1,4-diaminobutane bicarbonate.

3. The method according to claim 1, wherein the first composition is a fermented broth or a concentrate thereof.

4. The method according to claim 3, wherein the concentrate is prepared by concentrating the fermented broth at a vapor temperature in a range of about 10° C. to 100° C. and a pressure in a range of about 10 mmHg to about 760 mmHg.

5. The method according to claim 3, wherein the pH of the concentrate is 10.0 or higher.

6. The method according to claim 1, wherein 70 wt % or more of the carbonate salt of 1,4-diaminobutane comprised in the first composition is separated by the distillation.

7. The method according to claim 1, wherein the distillation is performed at a vapor temperature in a range of about 30° C. to 158° C. and a pressure in a range of about 10 mmHg to about 760 mmHg.

8. The method according to claim 1, wherein the pH of the second composition is 10.0 or higher.

9. The method according to claim 1, wherein the removing of the carbonate is performed by fractional distillation.

10. The method according to claim 9, wherein the fractional distillation is performed at a vapor temperature in a range of about 100° C. to 230° C. and a pressure in a range of about 1 atm to about 5 atm.

11. The method according to claim 9, wherein the fractional distillation is performed using a distillation tower.

12. The method according to claim 11, wherein the 1,4-diaminobutane is recovered from a lower part of the distillation tower, wherein the lower part of the distillation tower is disposed below a region into which the second composition is inserted into the distillation tower.

13. A method for purifying 1,4-diaminobutane comprising the steps of:
    culturing a microorganism producing 1,4-diaminobutane in a medium while being provided with a nitrogen source to produce carbonate salt of 1,4-diaminobutane;
    preparing a fermented broth or a concentrate thereof that comprises carbonate salt of 1,4-diaminobutane;
    separating a third composition comprising carbonate salt of 1,4-diaminobutane by distillation of the fermented broth or a concentrate thereof; and
    removing carbonate from the 1,4-diaminobutane carbonate comprised in the third composition to recover 1,4-diaminobutane, and
wherein the nitrogen source is at least one selected from ammonia, ammonium salt of an organic compound, and a carbonate-based inorganic compound.

14. The method according to claim 13, wherein the concentrate is prepared by concentrating the fermented broth at a vapor temperature in a range of about 10° C. to 100° C. and a pressure in a range of about 10 mmHg to about 760 mmHg.

15. The method according to claim 13, wherein the pH of the concentrate is 10.0 or higher.

16. The method according to claim 13, further comprising removing bacterial cells from the fermented broth before the separating of the third composition.

17. The method according to claim 13, wherein the carbonate salt of 1,4-diaminobutane comprises at least one of 1,4-diaminobutane carbonate and 1,4-diaminobutane bicarbonate.

18. The method according to claim 13, wherein 70 wt % or more of the carbonate salt of 1,4-diaminobutane comprised in the third composition is separated by the distillation.

19. The method according to claim 13, wherein the distillation is performed at a vapor temperature in a range of about 30° C. to 158° C. and a pressure in a range of about 10 mmHg to about 760 mmHg.

20. The method according to claim 13, wherein the pH of the third composition is 10.0 or higher.

21. The method according to claim 13, wherein the removing of the carbonate is performed by fractional distillation.

22. The method according to claim 21, wherein the fractional distillation is performed at a vapor temperature in a range of about 100° C. to 230° C. and a pressure in a range of about 1 atm to about 5 atm.

23. The method according to claim 21, wherein the fractional distillation is performed using a distillation tower.

24. The method according to claim 23, wherein the 1,4-diaminobutane is recovered from a lower part of the distillation tower, wherein the lower part of the distillation tower is disposed blow a region into which the third composition is inserted into the distillation tower.

* * * * *